(12) United States Patent
Basara (10) Patent No.: US 7,132,111 B2
(45) Date of Patent: *Nov. 7, 2006

(54) ODORLESS FORMULATION FOR TREATING MUCOSAL DISCONTINUITIES

(75) Inventor: Michael Basara, Hugo, MN (US)

(73) Assignee: Epien Medical, Inc., Minnetonka, MN (US)

( * ) Notice: Subject to any disclaimer, the term of this patent is extended or adjusted under 35 U.S.C. 154(b) by 484 days.

This patent is subject to a terminal disclaimer.

(21) Appl. No.: 10/443,446

(22) Filed: May 21, 2003

(65) Prior Publication Data

US 2004/0132810 A1 Jul. 8, 2004

Related U.S. Application Data

(60) Provisional application No. 60/437,777, filed on Jan. 3, 2003.

(51) Int. Cl.
*A61K 13/00* (2006.01)
*A61K 8/00* (2006.01)

(52) U.S. Cl. .................. 424/434; 424/401; 424/49

(58) Field of Classification Search .............. None
See application file for complete search history.

(56) References Cited

U.S. PATENT DOCUMENTS

| | | | | |
|---|---|---|---|---|
| 3,459,800 A | * | 8/1969 | Batlle et al. | 552/203 |
| 3,920,835 A | | 11/1975 | Van Scott et al. | |
| 3,984,556 A | | 10/1976 | Hardtmann | |
| 3,988,470 A | | 10/1976 | Van Scott et al. | |
| 4,080,212 A | * | 3/1978 | Takahashi | 106/35 |
| 4,082,841 A | * | 4/1978 | Pader | 424/50 |
| 4,144,325 A | | 3/1979 | Voyt | |
| 4,416,982 A | * | 11/1983 | Tsuda et al. | 435/11 |
| 5,688,995 A | | 11/1997 | Luther et al. | |
| 6,596,299 B1 | * | 7/2003 | Basara | 424/435 |
| 6,830,757 B1 | * | 12/2004 | Basara | 424/435 |
| 2004/0234490 A1 | | 11/2004 | Basara | |

FOREIGN PATENT DOCUMENTS

| GB | 820659 | 9/1959 |
|---|---|---|
| WO | WO-2004062580 A3 | 7/2004 |

OTHER PUBLICATIONS

Budavari, et al., *The Merck Index*, eleventh edition, (1989), 7212.
Forstner, J., et al., "Intestinal goblet cell mucus: isolation and identification by immunofluorescence of a goblet cell glycoprotein", *J Cell Sci.*, 12(2), (Mar. 1973), 585-602.
Lebat-Robert, J., et al., "Glycoproteines du mucus gastrique: structure, fonctions et pathologie", *Pathologie biologie*, 24, (1979), 241-247.
Lehr, C. M., et al., "Visualization studies of the mucoadhesive interface", *Journal of Controlled Release*, 18, (1992), 249-260.
Peppas, N., et al., "Suface, interfacial and molecular aspects of polymer bioadhesion on soft tissues", *Journal of Controlled Release*, 2, (1985), 257-275.
Spiro, R. G., "Glycoproteins", *Annu Rev Biochem.*, 39, (1970), 599-638.
"International Search Report and Written Opinion for Application No. PCT/US04/00133, date mailed Oct. 27, 2005", 11 Pages.

* cited by examiner

*Primary Examiner*—Gollamudi S. Kishore
*Assistant Examiner*—Pili A. Hawes
(74) *Attorney, Agent, or Firm*—Schwegman, Lundberg, Woessner & Kluth, P.A.

(57) ABSTRACT

The present invention includes a method for making a formulation for treating mucosal discontinuities, comprising: providing phenolic compounds and treating the purified phenolic compounds with sulfuric acid to make sulfonic acids and sulfonate salts. The present invention also includes formulations prepared by the method.

2 Claims, 7 Drawing Sheets

Fig-2

*Liquid Chemical Cauterization Agent for the Oral Cavity Mucosa*

- Mechanisms of Therapeutic Action
  - Solvent/Keratolytic
    - Penetrates/Dissolves Necrotic Tissues
  - Hygroscopic/Dehydrating
    - Reduces Tissue Edema
    - Solvation is Exothermic
    - Solvation Releases Acidification
  - Denaturant/Keratocoagulant
    - Acidification Necrosis and Oxidation
    - Surrogate Eschar/Clot = Protective Natural Bandage

- Features and Benefits
  - Virtually Instantaneous Pain Relief
  - Accelerated Ulcer Healing
  - Kills Infectious Organisms
  - One Time Treatment
  - Self-Limited Action/Not Harmful to Healthy Mucosa
    - Water Solvation Requirement
    - Barrier Membrane Formation
    - Acid Neutralization

Fig. 3

SPG-perio Formulation – (Rx Only)

Liquid Phenol USP, Guaiacol USP, Sulfuric Acid NF, Purified Water USP, FD&C Red #40

- Odor – Mild Phenolic
- Color – Purple
- Viscosity – 1025 cPs@25°C
- Total Acidity – 9.1 mM/g
- Density – 1.59 g/mL
- Application Time – 5 to 30+ seconds per pocket
- Applicator/Packaging – Pre-Filled Syringe/Procedure Pack
- Tissue Colorant – None
  - Composition (w/w)
    - Phenolsulfonic Acid – 30%
    - Guaiacolsulfonic Acid – 32%
    - Free Sulfuric Acid – 24%
    - Water – 11.9%
    - FD&C Red #40 – 0.075%

Fig. 4

SPG-gingivitis Formulation (Rx & OTC)

Liquid Phenol USP, Guaiacol USP, Sulfuric Acid NF, Purified Water USP, FD&C Colorant

- Odor – Mild Phenolic, Floral, Herbal
- Color - Gold, Red, Purple
- Viscosity - 70 to 1000+ cPs
- Total Acidity - 5.50 to 9.20 mM/g
- Density – 1.40 to 1.60 g/mL
- Application Time - 5 to 30+ seconds
- Applicator/Packaging - Vial, Syringe/Procedure Pak, Swab
- Tissue Colorant – None, Green, Blue

- Composition (w/w)
  - Phenolsulfonic Acid - 25% to 80%
  - Guaiacolsulfonic Acid - 25% to 80%
  - Ammonium Phenolsulfonate - 0% to 5%
  - Free Sulfuric Acid - 0% to 3.0%
  - Water - 13% to 30%
  - Colorant - 0.075% to 0.020% fig. 5

SPG-ras Formulation (Rx & OTC)

Liquid Phenol USP, Guaiacol USP, Sulfuric Acid NF, Purified Water USP, FD&C Colorant

- Odor – Mild Phenolic, Floral, Herbal
- Color - Gold, Red, Purple
- Viscosity - 70 to 1000+ cPs
- Total Acidity - 7.20 to 9.20 mM/g
- Density – 1.46 to 1.59 g/mL
- Application Time - 5 to 15+ seconds
- Applicator/Packaging - Vial, Pre-Filled Syringe, SwabPlus
- Tissue Colorant – None, Green, Blue

- Composition (w/w)
  - Phenolsulfonic Acid - 25% to 80%
  - Guaiacolsulfonic Acid - 25% to 80%
  - Ammonium Phenolsulfonate - 0% to 5%
  - Free Sulfuric Acid - 0% to 32%
  - Water - 13% to 30%
  - Colorant - 0.075% to 0.020%

ODORLESS FORMULATION FOR TREATING MUCOSAL DISCONTINUITIES

RELATED APPLICATIONS

Reference is made to the following commonly assigned application entitled as follows: METHOD FOR EXFOLIATING SKIN. The above-identified Application is being filed on May 21, 2003, the same filing date as the instant application.

This application claims priority from U.S. provisional application No. 60/437,777 filed Jan. 3, 2003, which application is incorporated herein by reference.

BACKGROUND

The present invention relates to an odorless formulation for treating mucosal discontinuities. The present invention also includes a method for making the formulation and a method for using the formulation.

The term, "mucosal discontinuities" as used herein refers to discontinuities which are present or which are inflicted on mucosal tissue of living beings. Mucosal discontinuities include wounds which are internal or external bodily injuries or lesions which are caused by a physical force or by another mechanism. The physical force is one or more of a mechanical, chemical, viral, bacterial, or thermally induced physical force. The physical force disrupts the normal continuities of biologic structures of living beings.

Mucosal discontinuities include contusions, wounds in which the skin is unbroken, incisions, wounds in which the skin is broken by a cutting instrument, lacerations, and wounds in which the skin is broken by a dull or blunt instrument. Discontinuities include wounds caused by accident or by surgical procedures.

Patients who suffer major wounds and other discontinuities benefit from treatment that enhances healing and pain relief. Wound healing mechanisms comprise a series of processes whereby tissue, such as mucosal tissue, is repaired. In particular, in repair, specialized tissue is regenerated. New tissue is reorganized.

Wound healing typically comprises three phases. A first phase is an inflammation phase that lasts up to about 3 days. A second phase is a cellular proliferation phase that lasts from about 3 to 12 days. A third phase is a remodeling phase that lasts from about 3 days to 6 months.

During the first inflammation phase, platelet aggregation and clotting form a matrix which traps plasma proteins and blood cells to induce the influx of various type of cells. During the second cellular proliferation phase, new connective or granulation tissue and blood vessels are formed. During the third remodeling phase, granulation tissue is replaced by a network of collagen and elastin fibers leading to the formation of scar tissue.

When cells are injured or killed as a result of a wound, the wound healing step is desirable to resuscitate the injured cells and to produce new cells to replace the dead cells. The healing process produces a reversal of cytotoxicity, a suppression of inflammation, and a stimulation of cellular viability and proliferation. Wounds typically require low levels of oxygen in the initial stages of healing to suppress oxidative damage and higher levels of oxygen in the later stages of healing to promote collagen formation by fibroblasts.

One type of mucosal discontinuity includes aphthous ulcers. Aphthous ulcers are believed to be caused by a virus, in some instances, as well as genetics, trauma, hormonal changes, and gastrointestinal factors.

Aphthous ulcers have shapes that range from single, multiple, round, to oval shaped. The ulcers range in size from 2–40 mm. The ulcers occur on mucus membranes of the tongue, cheeks, lips, soft and hard pallets, gingiva, pharynx and on the floor of the mouth. The ulcers are also found in the genital, anal, and in conjunctival mucosae.

Aphthous ulcers are extremely painful lesions. The ulcers appear as small macular red lesions. The ulcerated area quickly undergoes necrosis, leaving a sharply defined rounded ulcer, varying from about 2 to 5 mm in diameter. The ulceration is fairly deep with a yellow white base representing the tissue at the surface. The margin of the ulcer somewhat indurated and the margin of the mucosae has a surrounding erythematous zone. The marginal erythema ranges from slight to extensive, depending upon the degree of the secondary bacterial involvement.

The aphthous ulcer is present for about seven days and it undergoes gradual healing. It heals as a general rule in approximately 10–14 days and does not tend to leave a scar. Characteristically, there is a recurrent pattern of one of more of these ulcers. The ulcers recur as soon as one month apart and there are cases where, for a period of years, the individual is never without ulcers. New ulcers form as the existing lesions heal. In other cases, aphthous ulcer attacks may occur two to three times during a year. The lesions also often appear following some intense emotional stress, but they may first appear following a gradual change in environment or following an emotional situation in a non-familiar environment.

Aphthous ulcers have been found to occur in greater frequency in women. The ulcers appear several days prior to the menstrual period. The first encounter with aphthous stomatitis for women frequently follows the onset of menstruation. Women susceptible to these lesions often report freedom from the lesions during pregnancy. There is a tendency for a greater frequency of these lesions in females than in males. Although they occur at any age level, the ulcers occur more often in adults.

The term "Periadenitis Mucosa Necrotica Recurrens" is sometimes used to describe aphthae that coalesce to form an elongated, deep ulcerated area. From a symptomatic standpoint, it has found that about 24–48 hrs. before onset of an aphthous lesion, there is a vague discomfort, sometimes described as a tingling sensation in the area. As the tissue undergoes necrosis and an ulcer forms, the lesions become very painful. The aphthous lesions are often considered the most painful oral ulcerations. The discomfort may become particularly intense during periods of fatigue.

The histopathology of the disease is one where the microscopy picture is non-specific, generally showing an ulceration of the mucosae. The surface epithelium exhibits a central area of destruction. The connective tissue is densely infiltrated with lymphocytes, polymorphonuclear leukocytes, plasma cells, and histocytes. There is evidence of active fibrosis at the base and sides of the ulcerated area.

Differential diagnosis of aphthous ulcers includes traumatic ulcers, acute herpetic stomatitis, stomatitis medicamentosa, and erythema multiforme. The diagnosis of apthhous stomatitis is based upon the clinical manifestation and the patient's history. Biopsies are usually unnecessary due the extreme discomfort involved and are avoided unless necessary to rule out other lesions considered differentially diagnostic.

Many substances in agents have been used in an attempt to cure and or relieve the discomfort of aphthous lesion. For example, cauterizing drugs, such as phenol, chromic acid, alum and silver nitrate, have been used for many years. These agents alleviate pain by destruction of small nerve endings. The healing time of the lesion is prolonged due to the escharotic action of these drugs on the surface epithelium and the active fibrosis at the base and sides of the ulcerated areas. Vitamins have also been tried with inconsistent results. Antibiotics have been used with conflicting results.

One observer found that Aureomycin applied locally, three times a day appeared to have a definite effect. With treatment, the duration of the ulcers was reduced from about 10–5 days and there was an analgesic effect lasting one half to two hours. Temporary relief has also been sought and sometimes achieved by using milk of magnesia or heavy syrups. Other more exotic remedies have been tried with little or no success. These remedies include vaccination with cowpox virus, and nutrient supplements.

U.S. Pat. Nos. 3,920,835, 3,984,556, and 3,988,470, all issued to Van Scott et al., disclose methods for treating acne, dandruff and palmar keratosis, respectively. The methods generally comprise applying to an affected area a topical composition that comprises about 1% to 20% of a lower aliphatic compound composition that contains from 2 to 6 carbon atoms selected from a group consisting of alpha hydroxy acid, alpha-ketoacids and esters thereof, and 3-hydroxybutyric acid in a pharmaceutically acceptable carrier.

U.S. Pat. No. 4,416,982 issued to Tauda et al. discloses a method for decomposing hydrogen peroxide by reacting the hydrogen peroxide with a phenol or aniline derivative in the presence of peroxidase.

One prior art formulation is manufactured by Northern Research Laboratories of St. Paul, Minn. The formulation is a reddish-brown material that has a strong phenolic odor.

DESCRIPTION OF THE DRAWINGS

FIGS. 4–6 are descriptions of the attributes of the formulation of the present invention used to treat specified skin conditions.

FIG. 7 is a perspective view of devices for application of the formulation of the present invention.

SUMMARY

One embodiment of the present invention includes a method for making an array of formulations tailored for treating specific types of mucosal discontinuities. The method includes providing phenol, guaiacol, sulfuric acid and, optionally, water in preselected concentrations; reacting the guaiacol and phenol with the sulfuric acid and water to make phenolsulfonic acid and guaiacolsulfonic acid and, for some embodiments, free water and free acid to produce a formulation having a preselected concentration of preselected isomers of phenolsulfonic acid, preselected isomers of guaiacolsulfonic acid, and optionally, free acid and free water.

Another embodiment of the present invention includes a formulation for treating mucosal discontinuities, comprising: phenolsulfonic acid and isomers of phenolsulfonic acid; guaiacolsulfonic acid and isomers of guaiacolsulfonic acid and mono- and bis-forms of guaiacolsulfonic acid; ammonium phenolsulfonate; and potassium guaiacolsulfonate.

Another embodiment of the present invention includes a formulation for treating oral mucosal discontinuities, comprising: phenolsulfonic acid in a concentration of 25–80% by weight; guaiacolsulfonic acid in a concentration of 25–80% by weight; free sulfuric acid in a concentration of 13 to 32% by weight; and water in a concentration of 0 to 3% by weight.

One other embodiment includes a formulation for treating skin mucosal discontinuities, comprising: phenolsulfonic acid in a concentration of 25–80% by weight; ammonium phenolsulfonate in a concentration of 0 to 5% by weight; guaiacolsulfonic acid in a concentration of 25–80% by weight; free sulfuric acid in a concentration of 0 to 32% by weight; and water in a concentration of 0 to 3% by weight.

Another embodiment includes a device for treating mucosal discontinuities, comprising: a syringe, and the formulation of the present invention contained in the syringe.

One other embodiment of the present invention includes a system comprising: ingredients that include phenolsulfonic acid, guaiacolsulfonic acid, ammonium phenolsulfonate, potassium guaiacolsulfonate, water and free acid; and a mechanism calibrated to mix preselected amounts of two or more of the ingredients together to make a formulation for treating a specific type of mucosal discontinuity.

DETAILED DESCRIPTION

In its method and system aspects, the present invention includes a method and system for making an array of formulations tailored for treating specific types of mucosal discontinuities. The method includes providing phenol, guaiacol, sulfuric acid and, optionally, water, and reacting the guaiacol and phenol with the sulfuric acid and, optionally, water to make phenolsulfonic acid and guaiacolsulfonic acid and, for some embodiments, free water and free acid. The preselected concentrations of guaiacol, phenol, sulfuric acid, free acid and water produce a formulation having a preselected concentration of four isomers of phenolsulfonic acid, seven isomers of guaiacolsulfonic acid, and for some embodiments, free acid and free water. The specific isomer concentrations and concentration ratios are preselected by selecting specific reaction parameters such as time, temperature, and concentration of reactants that produce the preselected isomer concentration profile.

In another embodiment, the phenolsulfonic acid is further treated with a hydroxide such as ammonium hydroxide to make ammonium phenolsulfonate. The guaiacolsulfonic acid is treated with a hydroxide such as potassium or zinc hydroxide to make potassium guaiacolsulfonate.

The system of the present invention includes the ingredients phenolsulfonic acid, guaiacolsulfonic acid, sulfosalicylic acid, ammonium phenolsulfonate, potassium guaiacolsulfonate, water and sulfuric acid which is National Formulary (NF). The system also includes a mechanism calibrated to mix preselected amounts of the ingredients together to make a formulation for treating a specific type of mucosal discontinuity.

As used herein, the term "mucosal discontinuity" refers to lesions, ulceration, or inflammation on the moist linings of the buccal cavity, nasal cavity, gastrointestinal tract, respiratory tract, conjunctiva, vagina, colon, urinary bladder, and urethra (Forstner et al., 1973 J. Cell. Sci. 12:585; Peppas et al., 1985 J. Control. Release 2:257; Lehr et al., 1992 J. Control Release 18:249; Spiro, 1970 Ann. Rev. Biochem. 39:599; Lebat-Robert et al., 1979 Path. Biol. 24:241).

In one example, a formulation for treating gingivitis, one type of mucosal discontinuity, includes sulfonic acid and little or no free acid. In another example, phenolsulfonic acids and guaiacolsulfonic acids in a formulation with free sulfuric acid are used to treat periodontal disease, another type of mucosal discontinuity. In general, a formulation that includes phenolsulfonic acid, sulfosalicylic acid, and guaiacolsulfonic acid with no free acid is usable as a facial exfoliant or as a treatment for canker sores. A formulation that includes phenolsulfonic acid, sulfosalicylic acid, phenolsulfonate, and free acid is usable as a skin exfoliant for use on feet.

Figure 1A:
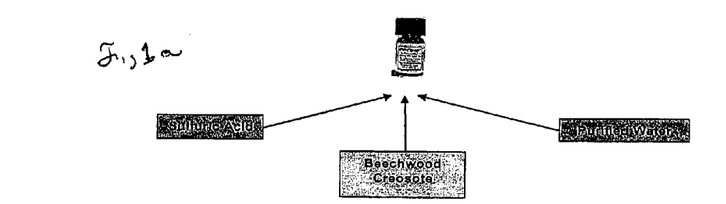
FIG. 1a is a schematic view of a prior art formulation that includes sulfuric acid, Beechwood creosote and purified water.
Figure 1B:
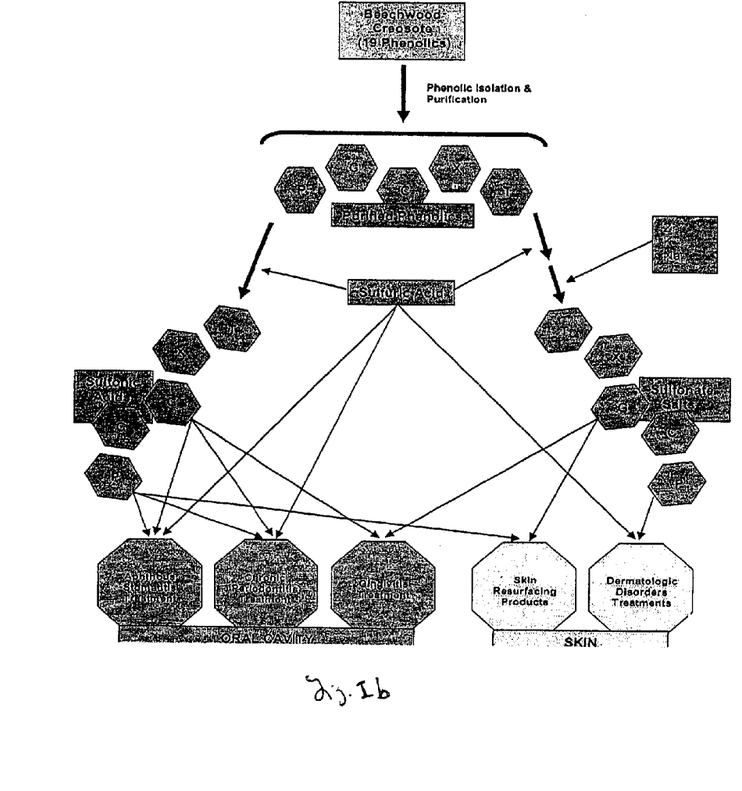
FIG. 1b is a schematic view of the formulation of the present invention and its uses in treating conditions of skin and the oral cavity.

In its product aspect, the present invention includes a formulation for treating mucosal discontinuities that includes phenolsulfonic acid, sulfosalicylic acid, guaiacolsulfonic acid, and, for some embodiments, ammonium phenolsulfonate, free sulfuric acid and water. In one embodiment, the formulation includes phenolic compounds that are isolated and purified, as is shown in FIG. 1B.

Figure 2:
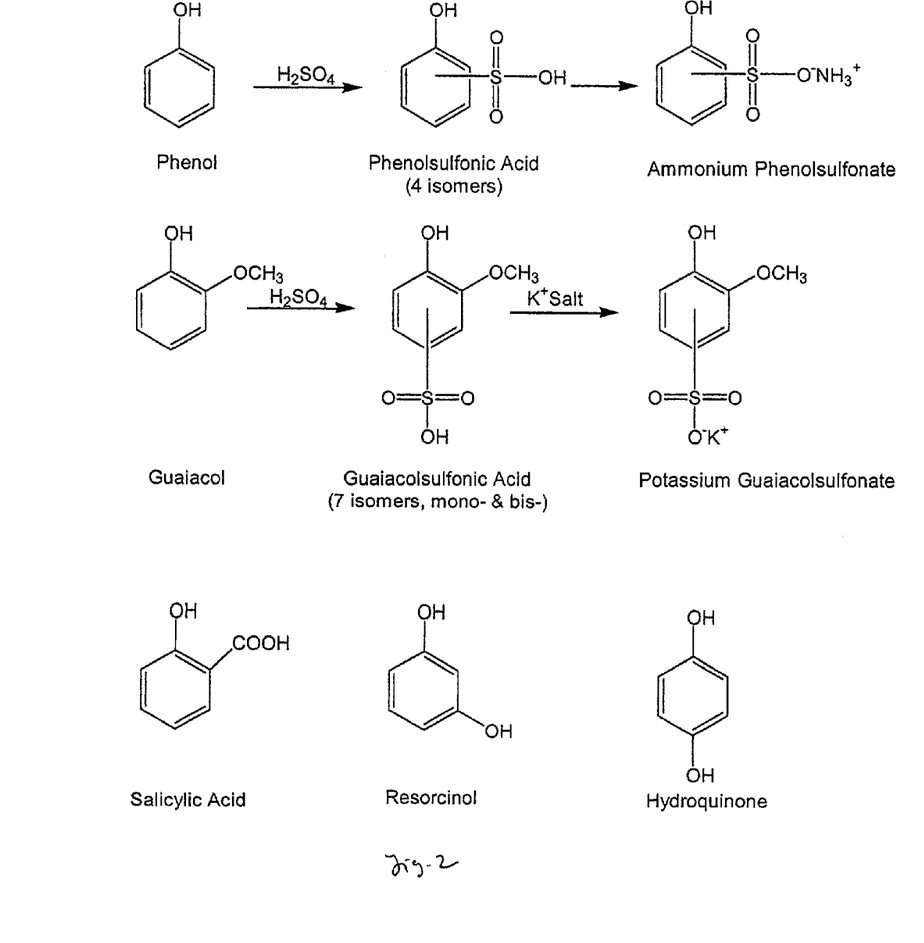
FIG. 2 is a formula view of chemicals in the formulation of the present invention.
Figure 3:
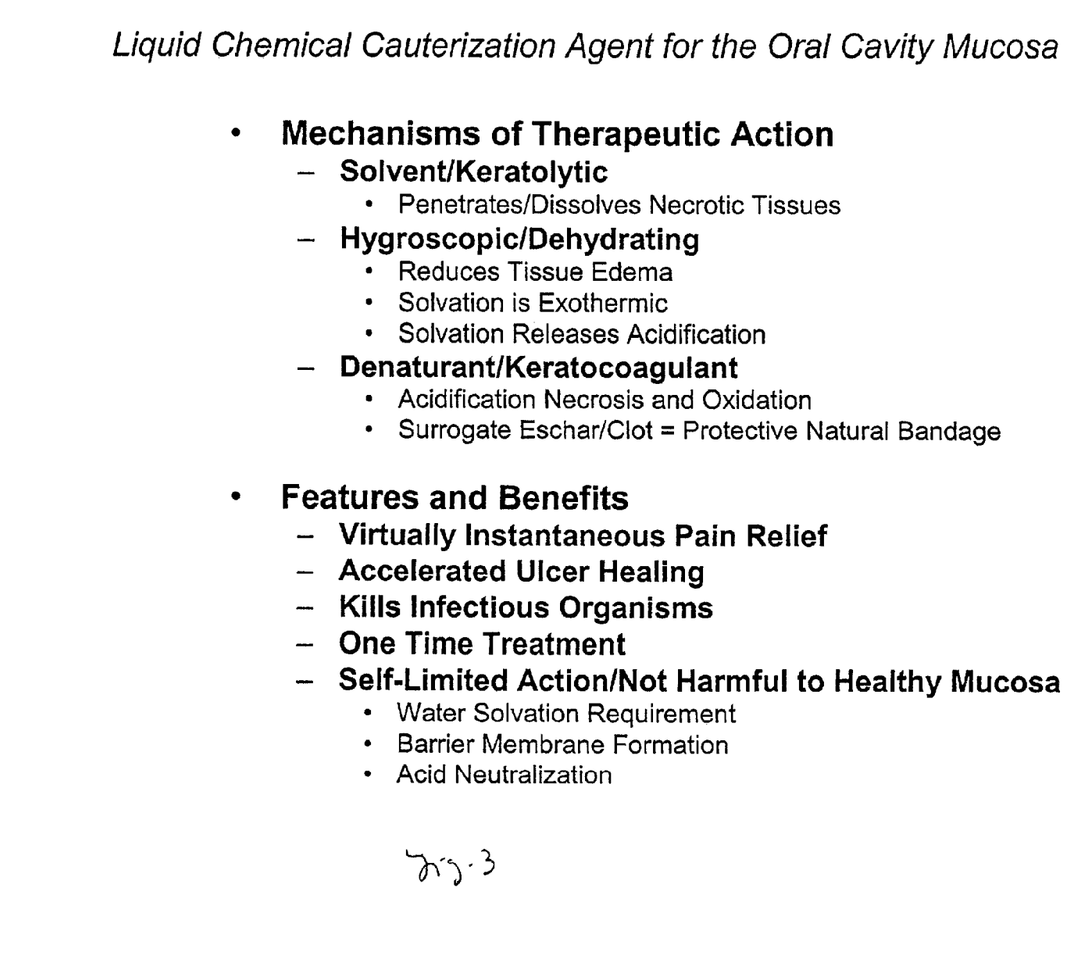
FIG. 3 is a description of attributes of the formulation of the present invention.

The purified phenolic compounds are shown in FIG. 2 and include phenol, guaiacol, salicylic acid, resorcinol and hydroquinone. The purified phenolics are treated with sulfuric acid to form sulfonic acids and sulfonate salts, as is shown in FIG. 1B. The sulfonate salts are treated with one or more of zinc, potassium and sodium to form a salt. Examples of other salts include alkali metal or alkaline earth metal salts and, particularly, calcium, magnesium, sodium, lithium, zinc, potassium, and iron salts. Phenolic compounds obtained from a variety of sources are usable to make the formulation of the present invention Formulations that include the sulfonic acids of phenol and guaiacol are used to treat mucosal discontinuities in the oral cavity such as aphthous stomatitis, canker sores, chronic periodontitis and gingivitis. Formulations that include the sulfonate salts of phenol and guaiacol are used to treat mucosal discontinuities of the skin, such as dermatologic disorders. Formulations that include the phenolsulfonate salts also have use as skin resurfacing products. A breakdown of these acid and salt products is shown in FIG. 2.

When phenol is treated with sulfuric acid, the reaction products include four isomers of phenolsulfonic acid. When guaiacol is treated with sulfuric acid, the reaction products include seven isomers, a mono- and a bis-form of guaiacolsulfonic acid. Other sources of phenolsulfonic acid include the four isomers. Other sources of guaicol include the seven isomers, a mono- and a bis-form of guaiacolsulfonic acid.

The method and system of the present invention is a significant improvement over methods and systems used to make formulations prepared with Beechwood creosote because the method, system, and formulations of the present invention do not have the intense phenolic odor and taste of prior art products. Furthermore, the efficacy of the formulations of the present invention is very high because the acids and salts are separated from Beechwood creosote and from each other or are synthesized in a process that does not require Beechwood creosote and are systematically and specifically blended in amounts that are targeted to treat the oral cavity and the skin, respectively.

Figure 4:
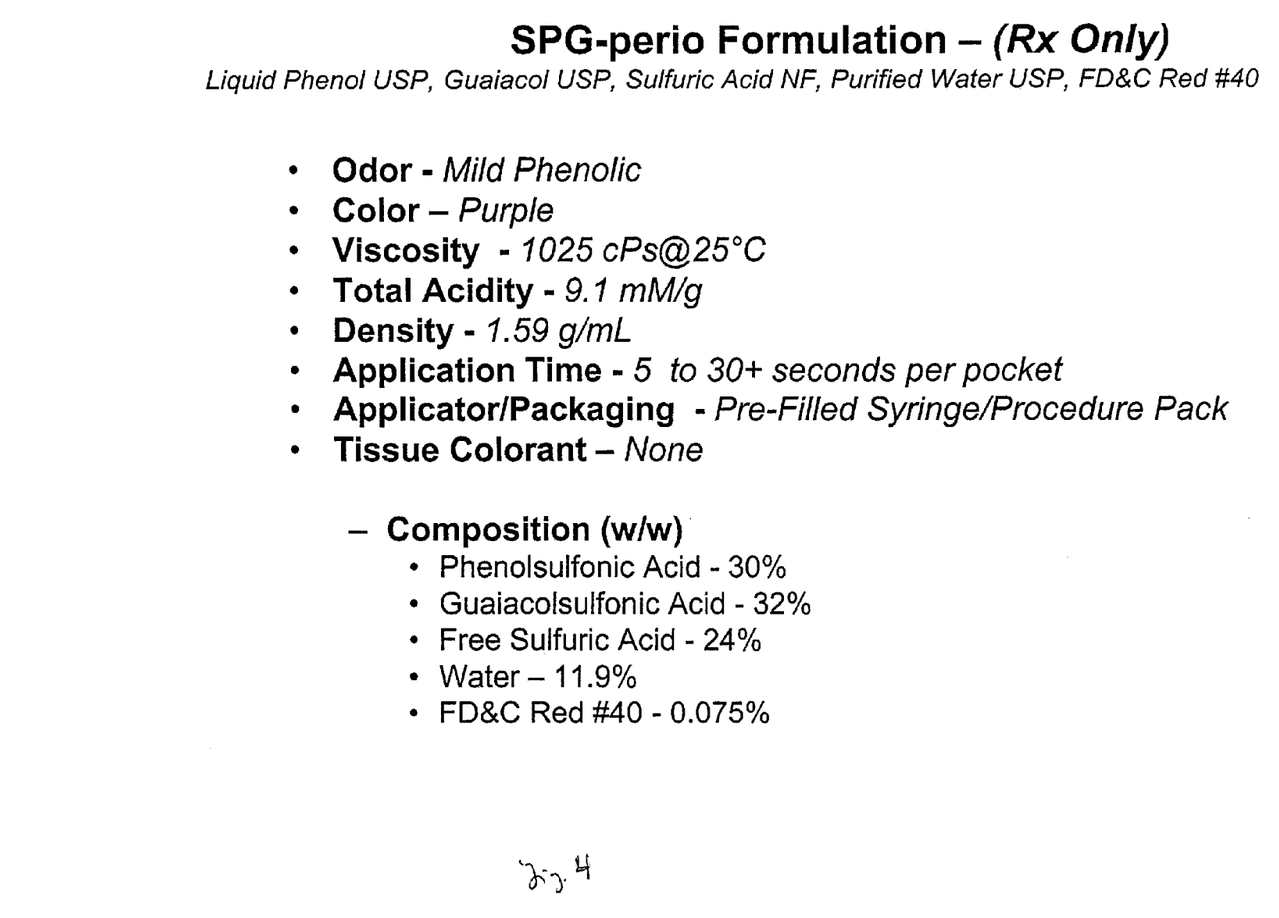
Figure 5:
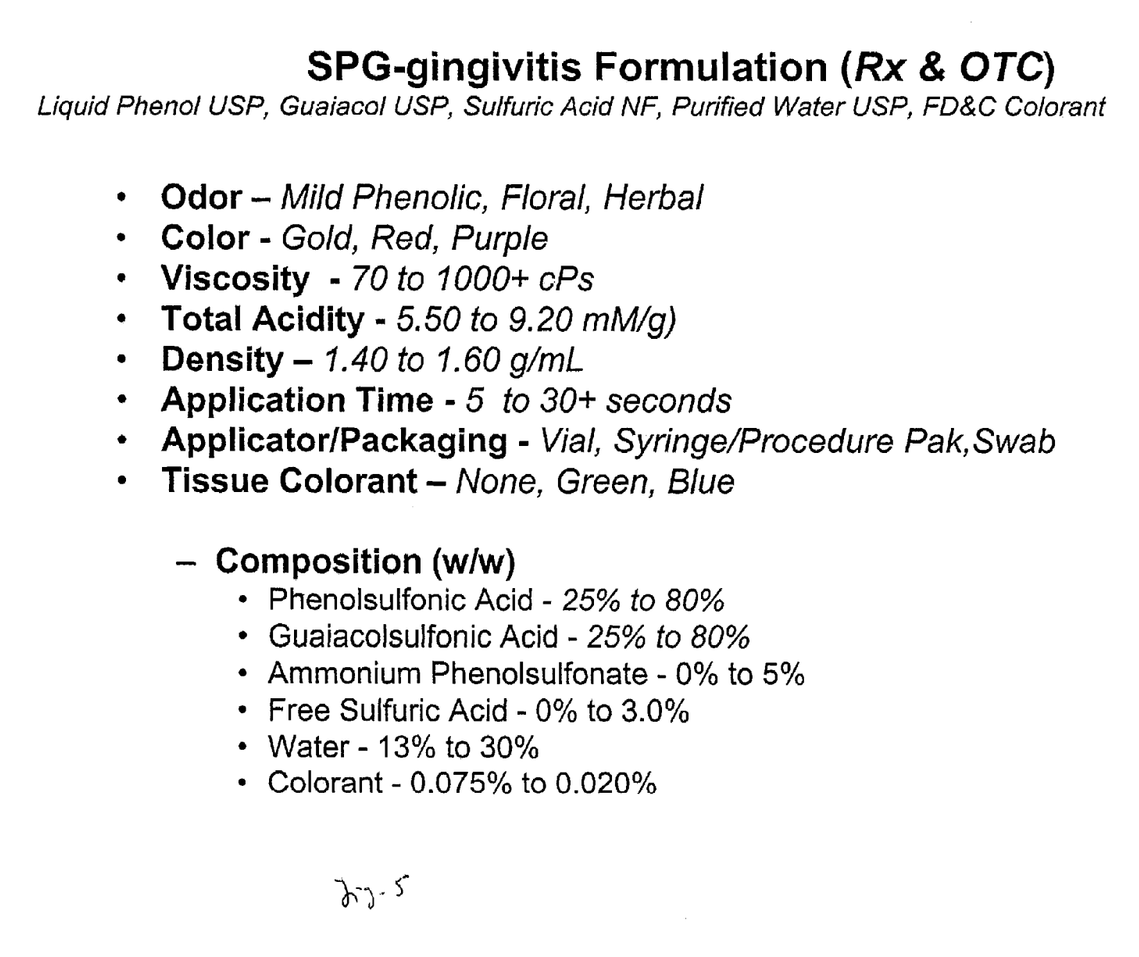
Figure 8:
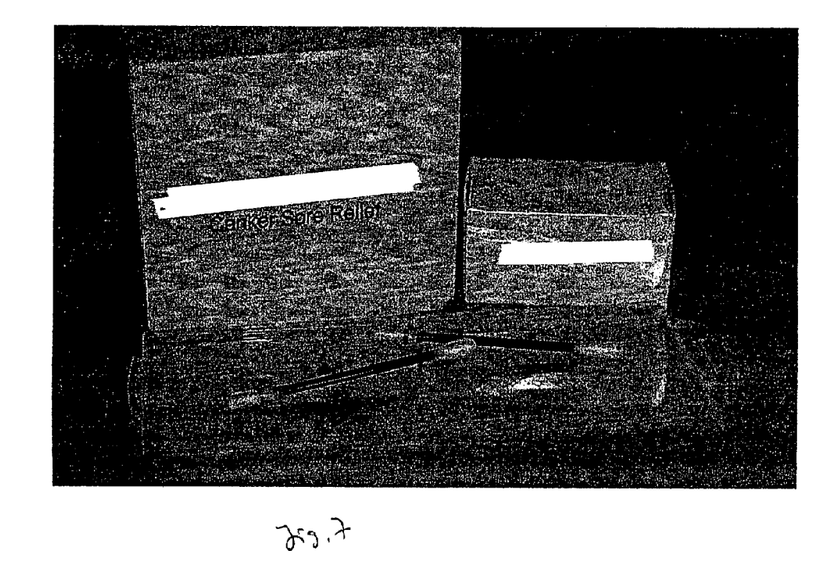

One formulation embodiment, for treating mucosal discontinuities of the oral cavity is described in FIG. 4. The formulation composition includes phenolsulfonic acid in a concentration of 30 percent by weight; guaiacolsulfonic acid in a concentration of 32 percent by weight; free sulfuric acid in a concentration of 24 percent by weight; water in a concentration of 11.9 percent by weight; and FD&C Red No. 40 in a concentration of 0.075 percent by weight. This formulation has a density of 1.59 g/mL, a total acidity of 9.1 mM/g, and a viscosity of 1025 cPs at 25 degrees Centigrade.

The formulation is applied with an applicator. The application contact time for treatment of periodontal disease is 5 to 30 seconds per infected tooth pocket. In one embodiment, the applicator is a pre-filled syringe. In another embodiment, the applicator is a kit that includes a topical anesthetic and an application device such as the pre-filled syringe. The topical local anesthetic is applied with any conventional applicator such as a cotton swab. As used herein, the term "local anesthetic" means any drug that provides local numbness or analgesia or any drug that provides a regional blockage of nociceptive pathways (afferent and/or efferent) and that is not an agonist or an antagonist of an opioid receptors. The local anesthetic can be any local anesthetic known or to be developed. Examples of local anesthetics suitable for use with the invention include: ambucaine, amolanone, amylcaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dyclonine, ecogonidine, ecogonine, euprocin, fenalcomine, formocaine, hexylcaine, hydroxyteteracaine, isobutyl p-aminobenzoate, leucinocaine, levoxadrol, lidocaine, mepivacaine, meprylcaine, metabutoxycaine, methyl chloride, myrtecaine, naepaine, octacaine, orthocaine, oxethazaine, parenthoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, or pharmaceutically-acceptable salts thereof, or mixtures thereof. The anesthetic is separately packaged for some embodiments and incorporated into the formulation for other embodiments.

Some kit and formulation embodiments include an analgesic. Examples of suitable analgesics include, but are not limited to, aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtohnetin guacil, antipyrine, antipyrine salicylate, antrafenine, apazone, aspirin, benorylate, benoxaprofen, benzpiperylon, benzydamine, bermoprofen, bromfenac, p-bromoacetanilide, 5-bromosalicylic acid acetate, bucetin, bufexamac, bumadizon, butacetin, calcium acetylsalicylate, carbamazepine, carbiphene, carsalam, chlorthenoxazin(e), choline salicylate, cinchophen, ciramadol, clometacin, clonixin, cropropamide, crotethamide, dexoxadrol difenamizole, difiunisal, dihydroxyaluminum acetylsalicy, late, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophcnetide, lefetamine, lomoxicam, loxoprofen, lysine acerylsalicylate, magnesium acetylsalicylate, methotrimeprazine, metofoline, mofezolac, morazone, morpholine salicylate naproxen, nefopam, nifenazone, 5'-nitro-2'-propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, propacetamol, propyphenazone, ramifenazone, rimazolium metilsulfate, salacetamide, salicin, salicylamide, salicylamide o-acetic acid, salicylsulfuric acid, salsalate, salverine, simetride, sodium salicylate, suprofen, talniflumate, tenoxicam, terofenamate, tetrandrine, tinoridine, tolfenamic acid, tramadol, tropesin, viminol, xenbucin, and zomepirac Acceptable component ranges for a formulation for treating mucosal discontinuities of the oral cavity, such as gingivitis, are as follows:

| Component | Concentration Ranges |
|---|---|
| Phenolsulfonic Acid | 25–80% by weight |
| Guaiacolsulfonic Acid | 25–80% by weight |
| Sulfosalicylic Acid | 0–30% by weight |
| Citric Acid | 0–30% by weight |
| Ammonium Phenolsulfonate | 0–32% by weight |
| Free Sulfuric Acid | 0–32% by weight |
| Water | 13–30% by weight |

Acceptable component ranges for a formulation for treating mucosal discontinuities of the skin are as follows:

| Component | Concentration Ranges |
|---|---|
| Phenolsulfonic Acid | 25–80% by weight |
| Guaiacolsulfonic Acid | 25–80% by weight |
| Ammonium Phenolsulfonate | 0–5% by weight |
| Free Sulfuric Acid | 0–3% by weight |
| Water | 0–30% by weight |
| Colorant | 0.075–0.020% by weight |

These mucosal discontinuities include sores such as canker sores.

Another formulation embodiment of the present invention is for treatment of periodontal disease. Acceptable concentration ranges are as follows:

| Component | Concentration Ranges |
|---|---|
| Phenolsulfonic Acid | 25 to 80% |
| Guaiacolsulfonic Acid | 25 to 80% |
| Ammonium Phenolsulfonate | 0 to 32% |
| Free Sulfuric Acid | 0 to 32% |
| Water | 0 to 30% |
| Colorant | 0.00 to 0.075% |

The viscosity is 70 to 1000 cPs. The total acidity is 7.20 to 9.20 mM/g. The density is 1.46 to 1.59 g/mL. The application time is 5 to at least 60 seconds. The applicator includes in some embodiments, a vial, a pre-filled syringe, or a swab or combinations of these applicators. The formulation optionally includes a colorant such as green or blue.

The formulation of the present invention has use as a liquid chemical cauterization agent for, in one embodiment, the oral cavity mucosa. The mechanisms of therapeutic action include solvent and keratolytic-based mechanisms that include penetrating and dissolving necrotic tissues. The mechanism also includes hygroscopic and dehydrating-based mechanisms. In particular, the formulation reduces tissue edema. The solvation is exothermic. The solvation releases acidification. The mechanism is also a denaturant and keratocoagulant-based. The formulation causes acidification necrosis and oxidation. The formulation also aids in generation of a surrogate Eschar/clot that acts as a protective natural bandage.

The formulation of the present invention provides instantaneous pain relief to a user and accelerates ulcer healing. The formulation kills infectious organisms and is effective in a single application applied to an ulcer or other mucosal discontinuity. The formulation of the present invention is self-limited and is not harmful to healthy mucosa. The reaction of the formulation is limited by water solvation, barrier membrane formation, and acid neutralization.

Devices for applying the formulations of the present invention are shown in FIG. 7 and include a syringe and a cotton swab. In one embodiment, the syringe is prefilled. In one embodiment, the formulation of the present invention is enclosed within a swab device. In another embodiment, the formulation is enclosed in a container with a delivery mechanism that delivers the formulation drop-by-drop. In another embodiment, the formulation is metered. In one other embodiment, the formulation is enclosed in a container that includes a mechanism for heating or cooling the formulation. The mechanism includes chemicals, separated in compartments by a breakable seal, adjacent to the formulation of the present invention, that create either an exothermic or endothermic reaction when combined. In one embodiment, the chemicals are separated from the formulation by a wall. The chemicals are combined when a user breaks the breakable seal. The heating or cooling is transferred to the formulation through the wall. The packaged formulation of the present invention is transported for sale to pharmacies and drug stores. In other embodiments, the formulation of the present invention is packaged with an anesthetic. The anesthetic is applied to the mucosal discontinuity first.

In its method aspect, one embodiment of the present invention includes a method for preparing treatments for mucosal discontinuities in the oral cavity and skin. One method embodiment is described in the following example:

EXAMPLE 1

Phenolsulfonic acid solution was prepared in sulfuric acid. The method included setting up a recirculating water bath so that the water was at a temperature of 95 degrees Centigrade. Next, the weight of available stock of Liquified Phenol USP containing 3.23 moles of Phenol was calculated. Phenol has a molecular weight of 94.11. The weight of 3.23 moles of Phenol is 3.23×94.11+303.97 grams. The purity of Liquified Phenol USP typically ranges from 89.0% to 91.5%. Using the purity value either from the manufacturer's Certificate of Analysis or the purity value from an internal quality control analysis, the weight of the available stock of Liquified Phenol USP required to deliver 3.23 moles of Phenol was calculated.

The amount of available stock sulfuric acid (NF) that contains 7.08 moles was calculated. The purity of sulfuric acid NF typically ranges from 95.0% to 98%. A 1 liter Corning Pyrex Bottle No. 1395 was placed on a Mettler PG-5002-S balance. A 600 mL beaker was filled with about 400 mL of Liquified Phenol USP from the stock bottle. A quantity of 3.23 moles of phenol as liquified phenol USP by weight was added from the beaker using the weight of available stock. The amount of liquid phenol was calculated to provide 3.23 moles of phenol.

About 400 mL of stock sulfuric acid NF were added to a 600 mL Pyrex beaker. With the 1 liter Corning bottle containing the Liquified Phenol still on the Mettler balance, 7.08 moles of sulfuric acid was added to the bottle as stock sulfuric acid NF by weight from the beaker using the weight of available stock sulfuric acid NF that was calculated to provide 7.08 moles of sulfuric acid.

A 5 cm magnetic stirring bar was placed in the bottle containing the phenol/sulfuric acid mixture. The bottle and mixture were enclosed with a standard Corning low-temperature closure, placed on the bottle. The mixture was mixed on a magnetic stir plate for thirty minutes. The bottle was placed in a pre-heated 95 degrees Centigrade recirculating water bath for 14 to 24 hours.

The bottle was removed from the water bath after 14 to 24 hours. The bottle was allowed to cool to room temperature and an identifying sticker was applied.

A solution of guaiacolsulfonic acid in sulfuric acid was prepared. Water in the recirculating water bath was heated to 65 degrees Centigrade. The weight of available stock guaiacol, purified reagent, that contained 1.63 moles of guaiacol was calculated. The amount of available stock of sulfuric acid NF that contained 3.41 moles of sulfuric acid was calculated. A 1 liter Corning Pyrix bottle No. 1395 was placed on the Mettler PG-5002-S balance. A 600 mL beaker was filled with approximately 400 mL guaiacol, purified reagent from the available stock bottle. A quantity of 1.63 moles of guaiacol as guaiacol, purified reagent by weight from the beaker was added to the bottle.

A 5 cm magnetic stir bar was placed in the bottom of the Pyrex bottle. The bottle was placed on a magnetic stir plate and stirred at low speed. A ring stand was placed next to the stir plate. A thermometer was mounted onto the ring stand so that the tip of the thermometer was positioned in the guaiacol. A 250 mL cylinder was also mounted onto the ring stand so that the tip was inserted into the opening of the Pyrex bottle.

A 600 mL Pyrex beaker was filled with approximately 400 mL of stock sulfuric acid NF. A second 600 mL beaker was placed on the Mettler PG-5002-S balance. A quantity of 3.41 moles of sulfuric acid as stock sulfuric acid NF was added to the second beaker. With the cylinder stopcock in the closed position, the weighed amount of sulfuric acid NF was transferred from the second beaker to the addition cylinder mounted above the Pyrex bottle containing the measured quantity of guaiacol. The sulfuric acid was added from the addition cylinder to the guaiacol in the bottle in 10 to 20 mL aliquots while maintaining steady stirring. The temperature of the mixture was monitored to maintain a range of 55 to 65 degrees Centigrade until all of the acid was placed in the bottle.

The reaction mixture was stirred for 30 minutes after all of the sulfuric acid was added to the mixture. The mixture was enclosed by a standard Corning low temperature closure on the bottle. The bottle was placed in a pre-heated 65 degrees Centigrade recirculating water bath for 14 to 24 hours. The bottle was removed after the 14 to 24 hours and allowed to come to room temperature. The bottle was then marked.

The phenolsulfonic acid solution and the guaiacolsulfonic acid solution were then subjected to quality control. After being release by Quality Control, 1000 grams of the phenolsulfonic acid solution and 500 grams of the guaiacolsulfonic acid solution were prepared in a 2 liter Corning Pyrix bottle No. 1395 using the Mettler PG-5002-S balance. A quantity of 1.125 grams of FD&C Red #40 powdered colorant was weighed and added to the phenolsulfonic/guaiacolsulfonic mixture. The bottle was mixed by inverting repeatedly until the color was evenly dispersed. The colored phenolsulfonic/guaiacolsulfonic mixture was then available for use.

EXAMPLE 2

A facial exfoliant was prepared. A solution of phenolsulfonic acid was prepared as described in Example 1, except that the weight of available stock liquefied phenol USP was calculated and prepared for 4.0 moles of phenol. The amount of available stock sulfuric acid NF that contained 4.0 moles was calculated. The weight of sulfuric acid NF was 392.32 grams. The 4.0 moles of sulfuric acid NF was treated as described in Example 1. A quantity of 400 mL of Liquified Phenol USP was added to a 600 mL beaker. A quantity of 4.0 moles of phenol as Liquefied Phenol USP was added to a 1 L Corning Pyrex No. 1395 bottle using the Mettler PS-5002-S balance.

A second 600 mL Pyrex beaker was filled with approximately 400 mL of stock sulfuric acid NF. With the 1 L Corning bottle containing the liquefied phenol still on the Mettler balance, 4.0 moles of sulfuric acid as stock sulfuric acid NF by weight, was added to the bottle.

A 5 cm magnetic stirring bar was placed in a bottle containing the phenol/sulfuric acid mixture and enclosed with a Corning low-temperature closure. The solution was mixed for 30 minutes. The bottle was then placed in a pre-heated 95 degree Centigrade recirculating water bath for 14 to 24 hours. After 14 to 24 hours, the bottle was removed and allowed to come to room temperature and marked with a sticker.

The weight of available stock guaiacol, purified reagent that contained 3.50 moles of guaiacol was calculated. The amount of available stock sulfuric acid NF that contained 3.50 moles of sulfuric acid was also calculated. A 1 L Corning Pyrex bottle No. 1395 was placed on the Mettler PG-5002-S balance. A 600 mL beaker was filled with approximately 400 mL of guaiacol, purified reagent. A quantity of 3.50 moles of guaiacol was added from the beaker to the 1 L Pyrex bottle. A quantity of 3.50 moles of sulfuric acid NF was added to the 1 L Pyrex bottle, as described in Example 1, in 10 to 20 mL aliquots while maintaining steady stirring between 55 to 65 degrees Centigrade until all of the acid had been placed in the bottle. The mixture was continuously stirred for 30 minutes after all of the sulfuric acid has been added and a Corning low temperature closure was placed on the bottle. The bottle was placed in a pre-heated 65 degree Centigrade recirculating water bath for 14 to 24 hours. The bottle was removed from the water bath after 14 to 24 hours. The bottle was allowed to come to room temperature and was then marked for quality control.

A quantity of 750 grams of the phenolsulfonic acid solution and 750 grams of the guaiacolsulfonic acid solution were combined in a 2 L Corning Pyrex bottle. A quantity of 1.5 grams of Citronellal fragrance was added. The acids were mixed by inverting the bottle repeatedly until evenly blended.

The method also includes treating the purified phenolics with sulfuric acid to make sulfonic acids and sulfonate salts. The method further includes using the sulfonic acids to treat mucosal discontinuities in the oral cavity such as aphthous stomatitis, chronic periodontitis, canker sores, and gingivitis. The method includes using the sulfonate salts to treat dermatologic disorders and for skin resurfacing.

EXAMPLE 3

A skin exfoliant for use on feet was prepared. A solution of phenolsulfonic acid was prepared as described in Example 1, except that the weight of available stock liquefied phenol USP was calculated and prepared for 5.0 moles of phenol. The amount of available stock sulfuric acid NF that contained 5.0 moles was calculated. The weight of sulfuric acid NF was 490.4 grams. The 5.0 moles of sulfuric acid NF was treated as described in Example 1. A quantity of 470.55 gms of Liquified Phenol USP was added to a 600 mL beaker. A quantity of 5.0 moles of phenol as Liquefied Phenol USP was added to a 1 L Corning Pyrex No. 1395 bottle using the Mettler PS-5002-S balance.

A second 600 mL Pyrex beaker was filled with approximately 400 mL of stock sulfuric acid NF. With the 1 L Corning bottle containing the liquefied phenol still on the Mettler balance, 5.0 moles of sulfuric acid as stock sulfuric acid NF by weight, was added to the bottle.

A 5 cm magnetic stirring bar was placed in a bottle containing the phenol/sulfuric acid mixture and was enclosed with a Corning low-temperature closure. The solution was mixed for 30 minutes. The bottle was then placed in a pre-heated 95 degree Centigrade recirculating water bath for 14 to 24 hours. After 14 to 24 hours, the bottle was removed and was allowed to come to room temperature and marked with a sticker.

The phenolsulfonic acid and beaker were placed on the Mettler balance. A quantity of 300 grams of reagent grade ammonium phenolsulfonate was added to the phenolsulfonic acid. A quantity of 30 grams of reagent grade zinc phenolsulfonate was added to the phenolsulfonic acid. A quantity of 1.5 grams of Citronellal fragrance was added. The acids were mixed by vigorous stirring using a power hand blender.

EXAMPLE 4

A treatment for canker sores was formulated. A solution of phenolsulfonic acid was prepared as described in Example 1, except that the weight of available stock liquefied phenol USP was calculated and prepared for 2.4 moles of phenol. The amount of available stock sulfuric acid NF that contained 5.26 moles was calculated. The weight of sulfuric acid NF was 515.90 grams. The 5.26 moles of sulfuric acid NF was treated as described in Example 1. A quantity of 400 mL of Liquified Phenol USP was added to a 600 mL beaker. A quantity of 2.4 moles of phenol as Liquefied Phenol USP was added to a 1 L Corning Pyrex No. 1395 bottle using the Mettler PS-5002-S balance.

A second 600 mL Pyrex beaker was filled with approximately 400 mL of stock sulfuric acid NF. With the 1 L Corning bottle containing the liquefied phenol still on the Mettler balance, 5.26 moles of sulfuric acid as stock sulfuric acid NF by weight, was added to the bottle.

A 5 cm magnetic stirring bar was placed in a bottle containing the phenol/sulfuric acid mixture and enclosed with a Corning low-temperature closure. The solution was mixed for 30 minutes. The bottle was then placed in a pre-heated 95 degree Centigrade recirculating water bath for 14 to 24 hours. After 14 to 24 hours, the bottle was removed and allowed to come to room temperature and marked with a sticker.

The weight of available stock guaiacol, purified reagent that contains 2.3 moles of guaiacol was calculated. The amount of available stock sulfuric acid NF that contains 4.82 moles of sulfuric acid was also calculated. A 1 L Corning Pyrex bottle No. 1395 was placed on the Mettler PG-5002-S balance. A 600 mL beaker was filled with approximately 400 mL of guaiacol, purified reagent. A quantity of 2.3 moles of guaiacol was added from the beaker to the 1 L Pyrex bottle. A quantity of 4.82 moles of sulfuric acid NF was added to the 1 L Pyrex bottle, as described in Example 1, in 10 to 20 mL aliquots while maintaining steady stirring between 55 to 65 degrees Centigrade until all of the acid had been placed in the bottle. Stirring was continued for 30 minutes after all of the sulfuric acid has been added and a Corning low temperature closure was placed on the bottle. The bottle was placed in a pre-heated 65 degree Centigrade recirculating water bath for 14 to 24 hours. The bottle was removed from the water bath after 14 to 24 hours. The bottle was allowed to come to room temperature and then was marked for quality control.

A quantity of 750 grams of the phenolsulfonic acid solution and 750 grams of the guaiacolsulfonic acid solution were combined in a 2 L Corning Pyrex bottle. A quantity of 1.5 grams of Citronellal fragrance was added. The acids were mixed by inverting the bottle repeatedly until evenly blended.

The method also includes treating the purified phenolics with sulfuric acid to make sulfonic acids and sulfonate salts. The method further includes using the sulfonic acids to treat mucosal discontinuities in the oral cavity such as aphthous stomatitis, chronic periodontitis and gingivitis. The method includes using the sulfonate salts to treat dermatologic disorders and for skin resurfacing.

Since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes, which come within the meaning and range of equivalency of the claims, are intended to be embraced therein.

The invention claimed is:

1. A formulation for treating oral mucosal discontinuities, comprising:
   phenolsulfonic acid in a concentration of 25–80% by weight;
   guaiacolsulfonic acid in a concentration of 25–80% by weight;
   free sulfuric acid in a concentration of 0 to 32% by weight; and
   water in a concentration of 0 to 3% by weight.

2. A formulation for treating skin mucosal discontinuities, comprising:
   phenolsulfonic acid in a concentration of 25–80% by weight;
   ammonium phenolsulfonate in a concentration of 0 to 5% by weight;
   guaiacolsulfonic acid in a concentration of 25–80% by weight;
   free sulfuric acid in a concentration of 0 to 32% by weight; and
   water in a concentration of 0 to 3% by weight.

* * * * *